United States Patent [19]

Birkenmeyer et al.

[11] Patent Number: 5,667,974
[45] Date of Patent: Sep. 16, 1997

[54] METHOD FOR DETECTING NUCLEIC ACID SEQUENCES USING COMPETITIVE AMPLIFICATION

[75] Inventors: Larry Birkenmeyer, Chicago; Isa K. Mushahwar, Grayslake, both of Ill.

[73] Assignee: Abbott Laboratories, Abbott Park, Ill.

[21] Appl. No.: 480,220

[22] Filed: Jun. 7, 1995

[51] Int. Cl.$^6$ .............................. C12Q 1/68; C12P 19/34; C07H 21/04
[52] U.S. Cl. ........................ 435/6; 536/24.3; 435/91.2
[58] Field of Search ................... 536/24.3; 435/91.2, 435/6

[56] References Cited

U.S. PATENT DOCUMENTS

| | | | |
|---|---|---|---|
| 5,219,727 | 6/1993 | Wang et al. | 435/6 |
| 5,427,930 | 6/1995 | Birkenmeyer et al. | 435/91.52 |

FOREIGN PATENT DOCUMENTS

| | | | |
|---|---|---|---|
| 0473155 | 3/1992 | European Pat. Off. | |
| 0593789 | 4/1994 | European Pat. Off. | |
| 9300447 | 1/1993 | WIPO | C12Q 1/68 |
| 9302215 | 2/1993 | WIPO | |
| 9320227 | 10/1993 | WIPO | |
| 9408087 | 4/1994 | WIPO | |
| 9502690 | 1/1995 | WIPO | |
| 9640996 A1 | 12/1996 | WIPO | |

OTHER PUBLICATIONS

P. Fang et al: "Simultaneous Analysis of Mutant and Normal Alleles for Multiple Cystic Fibrosis Mutations by the Ligase Chain Reaction." Human Mutation 6:144–157 (1995).

B. Goswami et al., "Competitor Template RNA For Detection and Quantitation of Hepatitis A Virus by PCR," Biotechniques 16(1): 114–121 (1994).

*Primary Examiner*—Stephanie W. Zitomer
*Assistant Examiner*—Joyce Tung
*Attorney, Agent, or Firm*—Priscilla E. Porembski

[57] ABSTRACT

The present invention provides a method for quantitatively detecting the amount of a target nucleic acid sequence which may be present in a test sample. A test sample which may contain a target nucleic acid sequence comprising target sequences X and Y is contacted with two primer sets, the first set being specific for target X and the second set being specific for target Y. The test sample also is contacted at the same time with an internal standard sequence IS, which is substantially derived from a combination of the first and second target sequences, and its corresponding oligonucleotide primers. Haptens are associated with the oligonucleotide primer sets in such a way that amplified target sequence products X and Y are detected by capture on a solid phase to which anti-hapten capture reagents are attached. A signal ratio of (X+Y)/S is determined to quantitate the amount of the target nucleic acid sequence contained in the sample.

8 Claims, 1 Drawing Sheet

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 46 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:1:

```
TAGGACCCCT  GCTCGTGTTA  CAGGCGGGGT  TTTTCTTGTT  GACAAG                    46
```

( 2 ) INFORMATION FOR SEQ ID NO:2:

( i ) SEQUENCE CHARACTERISTICS:
        ( A ) LENGTH: 46 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:2:

```
CCGTTTCTCC  TGGCTCAGTT  TACTAGTGCC  ATTTGTTCAG  TGGTTC                    46
```

( 2 ) INFORMATION FOR SEQ ID NO:3:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( i i ) MOLECULE TYPE: synthetic DNA ( i x ) FEATURE:
   ( A ) NAME/KEY: 5'biotin
   ( B ) LOCATION: 1

( x i ) SEQUENCE DESCRIPTION: SEQ ID NO:3:

TAGGACCCCT GCTCGTGTTA CA            22

( 2 ) INFORMATION FOR SEQ ID NO:4:

( i ) SEQUENCE CHARACTERISTICS:
   ( A ) LENGTH: 19 base pairs
   ( B ) TYPE: nucleic acid
   ( C ) STRANDEDNESS: single
   ( D ) TOPOLOGY: linear ( i i ) MOLECULE TYPE: synthetic DNA ( i x ) FEATURE:
   ( A ) NAME/KEY: 5'phosphate
   ( B ) LOCATION: 1

( i x ) FEATURE:
   ( A ) NAME/KEY: 3'biotin
   ( B ) LOCATION: 19

( x i ) SEQUENCE DESCRIPTION: SEQ ID NO:4:

AACACGAGCA GGGGTCCTA            19

( 2 ) INFORMATION FOR SEQ ID NO:5:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( i i ) MOLECULE TYPE: synthetic DNA ( i x ) FEATURE:
   ( A ) NAME/KEY: 5'phosphate
   ( B ) LOCATION: 1

( i x ) FEATURE:
   ( A ) NAME/KEY: 3'fluorescein
   ( B ) LOCATION: 22

( x i ) SEQUENCE DESCRIPTION: SEQ ID NO:5:

CGGGGTTTTT CTTGTTGACA AG            22

( 2 ) INFORMATION FOR SEQ ID NO:6:

( i ) SEQUENCE CHARACTERISTICS:
   ( A ) LENGTH: 24 base pairs
   ( B ) TYPE: nucleic acid
   ( C ) STRANDEDNESS: single
   ( D ) TOPOLOGY: linear ( i i ) MOLECULE TYPE: synthetic DNA ( i x ) FEATURE:
   ( A ) NAME/KEY: 5'fluorescein
   ( B ) LOCATION: 1

( x i ) SEQUENCE DESCRIPTION: SEQ ID NO:6:

CTTGTCAACA AGAAAAACCC CGCC                                                    24

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: synthetic DNA (ix) FEATURE:
        (A) NAME/KEY: 5'adamantane
        (B) LOCATION: 1

(xi) SEQUENCE DESCRIPTION: SEQ ID NO:7:

CCGTTTCTCC TGGCTCAGTT TAC                                                     23

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: synthetic DNA (ix) FEATURE:
        (A) NAME/KEY: 5'phosphate
        (B) LOCATION: 1

(ix) FEATURE:
        (A) NAME/KEY: 3'adamantane
        (B) LOCATION: 21

(xi) SEQUENCE DESCRIPTION: SEQ ID NO:8:

AAACTGAGCC AGGAGAAACG G                                                       21

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (ix) FEATURE:
        (A) NAME/KEY: 5'phosphate
        (B) LOCATION: 1

(ix) FEATURE:
        (A) NAME/KEY: 3'fluorescein
        (B) LOCATION: 22

(xi) SEQUENCE DESCRIPTION: SEQ ID NO:9:

AGTGCCATTT GTTCAGTGGT TC                                                      22

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: synthetic DNA (ix) FEATURE:
        (A) NAME/KEY: 5'fluorescein ( B ) LOCATION: 1

( x i ) SEQUENCE DESCRIPTION: SEQ ID NO:10:

GAACCACTGA ACAAATGGCA CTA                                    23

( 2 ) INFORMATION FOR SEQ ID NO:11:

( i ) SEQUENCE CHARACTERISTICS:
            ( A ) LENGTH: 45 base pairs
            ( B ) TYPE: nucleic acid
            ( C ) STRANDEDNESS: single
            ( D ) TOPOLOGY: linear ( i i ) MOLECULE TYPE: synthetic DNA ( x i ) SEQUENCE DESCRIPTION: SEQ ID NO:11:

TAGGACCCCT GCTCGTGTTA CAGTAAACTG AGCCAGGAGA AACGG             45

( 2 ) INFORMATION FOR SEQ ID NO:12:

( i ) SEQUENCE CHARACTERISTICS:
            ( A ) LENGTH: 45 base pairs
            ( B ) TYPE: nucleic acid
            ( C ) STRANDEDNESS: double
            ( D ) TOPOLOGY: linear ( i i ) MOLECULE TYPE: genomic DNA ( x i ) SEQUENCE DESCRIPTION: SEQ ID NO:12:

CTGTACCAAA CCTTCGGACG GAAATTGCAC CTGTATTCCC ATCCC             45

( 2 ) INFORMATION FOR SEQ ID NO:13:

( i ) SEQUENCE CHARACTERISTICS:
            ( A ) LENGTH: 45 base pairs
            ( B ) TYPE: nucleic acid
            ( C ) STRANDEDNESS: double
            ( D ) TOPOLOGY: linear ( i i ) MOLECULE TYPE: genomic DNA ( x i ) SEQUENCE DESCRIPTION: SEQ ID NO:13:

CTGTACCAAA CCTTCGGACA GAAATTGCAC CTGTATTCCC ATCCC             45

( 2 ) INFORMATION FOR SEQ ID NO:14:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: synthetic DNA ( i x ) FEATURE:
            ( A ) NAME/KEY: 5'fluorescein
            ( B ) LOCATION: 1

( x i ) SEQUENCE DESCRIPTION: SEQ ID NO:14:

CTGTACCAAA CCTTCGGAC                                         19

( 2 ) INFORMATION FOR SEQ ID NO:15:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: synthetic DNA ( i x ) FEATURE:
    ( A ) NAME/KEY: 5'phosphate
    ( B ) LOCATION: 1

( i x ) FEATURE:
    ( A ) NAME/KEY: 3'fluorescein
    ( B ) LOCATION: 18

( x i ) SEQUENCE DESCRIPTION: SEQ ID NO:15:

TCCGAAGGTT TGGTACAG      18

( 2 ) INFORMATION FOR SEQ ID NO:16:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: synthetic DNA ( i x ) FEATURE:
    ( A ) NAME/KEY: 5'phosphate
    ( B ) LOCATION: 1

( i x ) FEATURE:
    ( A ) NAME/KEY: 3'biotin
    ( B ) LOCATION: 24

( x i ) SEQUENCE DESCRIPTION: SEQ ID NO:16:

AAATTGCACC TGTATTCCCA TCCC      24

( 2 ) INFORMATION FOR SEQ ID NO:17:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: synthetic DNA ( i x ) FEATURE:
    ( A ) NAME/KEY: 5'biotin
    ( B ) LOCATION: 1

( x i ) SEQUENCE DESCRIPTION: SEQ ID NO:17:

GGGATGGGAA TACAGGTGCA ATTTC      25

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: synthetic DNA ( i x ) FEATURE:
    ( A ) NAME/KEY: 5'fluorescein
    ( B ) LOCATION: 1

( x i ) SEQUENCE DESCRIPTION: SEQ ID NO:18:

CTGTACCAAA CCTTCGGACA      20

( 2 ) INFORMATION FOR SEQ ID NO:19:

( i ) SEQUENCE CHARACTERISTICS:
    ( A ) LENGTH: 44 base pairs
    ( B ) TYPE: nucleic acid (C) STRANDEDNESS: double
                (D) TOPOLOGY: linear (ii) MOLECULE TYPE: genomic DNA (xi) SEQUENCE DESCRIPTION: SEQ ID NO:19:

TGTGCCTTGG GTGGCTTTGG GGCATGGACA TTGACCCTTA TAAA        44

(2) INFORMATION FOR SEQ ID NO:20:

(i) SEQUENCE CHARACTERISTICS:
                (A) LENGTH: 44 base pairs
                (B) TYPE: nucleic acid
                (C) STRANDEDNESS: double
                (D) TOPOLOGY: linear (ii) MOLECULE TYPE: genomic DNA (xi) SEQUENCE DESCRIPTION: SEQ ID NO:20:

TGTGCCTTGG GTGGCTTTAG GACATGGACA TTGACCCTTA TAAA        44

(2) INFORMATION FOR SEQ ID NO:21:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: synthetic DNA (ix) FEATURE:
                (A) NAME/KEY: 5'fluorescein
                (B) LOCATION: 1

(xi) SEQUENCE DESCRIPTION: SEQ ID NO:21:

TGTGCCTTGG GTGGCTTTG        19

(2) INFORMATION FOR SEQ ID NO:22:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: synthetic DNA (ix) FEATURE:
                (A) NAME/KEY: 5'phosphate
                (B) LOCATION: 1

(ix) FEATURE:
                (A) NAME/KEY: 3'fluorescein
                (B) LOCATION: 18

(xi) SEQUENCE DESCRIPTION: SEQ ID NO:22:

AAAGCCACCC AAGGCACA        18

(2) INFORMATION FOR SEQ ID NO:23:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: synthetic DNA (ix) FEATURE:
                (A) NAME/KEY: 5'phosphate
                (B) LOCATION: 1

(ix) FEATURE:
(A) NAME/KEY: 3'adamantane
(B) LOCATION: 22

(xi) SEQUENCE DESCRIPTION: SEQ ID NO:23:

CATGGACATT GACCCTTATA AA    22

(2) INFORMATION FOR SEQ ID NO:24:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: synthetic DNA (ix) FEATURE:
(A) NAME/KEY: 5'adamantane
(B) LOCATION: 1

(xi) SEQUENCE DESCRIPTION: SEQ ID NO:24:

TTTATAAGGG TCAATGTCCA TGCCC    25

(2) INFORMATION FOR SEQ ID NO:25:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: synthetic DNA (ix) FEATURE:
(A) NAME/KEY: 5'fluorescein
(B) LOCATION: 1

(xi) SEQUENCE DESCRIPTION: SEQ ID NO:25:

TGTGCCTTGG GTGGCTTTA    19

(2) INFORMATION FOR SEQ ID NO:26:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:26:

GGGATGGGAA TACAGGTGCA ATTTCGGGCA TGGACATTGA CCCTTATAAA    50

METHOD FOR DETECTING NUCLEIC ACID SEQUENCES USING COMPETITIVE AMPLIFICATION

FIELD OF THE INVENTION

The present invention relates to a method for amplifying and detecting a nucleic acid sequence which may be present in a test sample, and in particular, to a method for quantitatively detecting a nucleic acid sequence which may be present in a test sample.

BACKGROUND OF THE INVENTION

Methods for amplifying a target nucleic acid sequence that may be present in a test sample are, by now, well known in the art. Such methods include the polymerase chain reaction (PCR) and ligase chain reaction (LCR). These methods have found widespread application in the medical diagnostic field as well as the fields of genetics, molecular biology and biochemistry.

In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to geometrically increase the number of target sequence molecules. PCR is disclosed in U.S. Pat. Nos. 4,683,195 and 4,683,202.

LCR is an alternative mechanism for target amplification. In LCR, two sense (first and second) probes and two antisense (third and fourth) probes are employed in excess over the target. The first probe hybridizes to a first segment of the target strand and the second probe hybridizes to a second segment of the target strand, the first and second segments being positioned adjacent to each other so that the primary probes can be ligated into a fused product. Further, a third (secondary) probe can hybridize to a portion of the first probe and a fourth (secondary) probe can hybridize to a portion of the second probe in a similar ligatable fashion. If the target is initially double stranded, the secondary probes will also hybridize to the target complement in the first instance. Once the fused strand of sense and antisense probes are separated from the target strand, it will hybridize with the third and fourth probes which can be ligated to form a complementary, secondary fused product. The fused products are functionally equivalent to either the target or its complement. By repeated cycles of hybridization and ligation, amplification of the target sequence is achieved. This technique is described in EP-A-320,308, hereby incorporated by reference. Other aspects of LCR technique such as gap LCR (GLCR) are disclosed in EP-A-439,182, to K. C. Backman et al., hereby incorporated by reference.

Unfortunately, one drawback of nucleic acid amplification reactions is that they are mostly qualitative. The nature of amplification reactions makes it difficult for them to be used to quantitatively detect the presence of a target sequence which may be present in a test sample. Accordingly, while traditional amplification reactions are useful for detecting the presence of a minute quantity of a target sequence in a test sample, traditional amplification reactions generally cannot be employed to determine the quantity of a target sequence in a test sample.

Some traditional amplification reactions have been modified to enable quantitative amplification reaction analysis. One such quantitative amplification reaction is called "competitive amplification." This method is commonly applied to PCR. According to this method, a standard nucleic acid sequence competes with a target sequence during the amplification reaction. Generally, the standard sequence and a sample suspected of containing a target sequence are combined in a dilution series in which the amount of the standard sequence is constant in all members of the series. Alternatively, the standard sequence and sample sequence are combined in a dilution series in which the amount of standard sequence is varied among the members of the dilution series. In any case, the concentration of the standard sequence in the members of the dilution series is known. PCR is then performed on all members of the dilution series and results in the production of a mixture of two nucleic acid species. One species is derived from the standard sequence and one species is derived from the sample sequence. The concentration of each species in a particular dilution depends on the number of copies of the standard and the sample sequences in the dilution prior to amplification. During the amplification reaction, detectable groups are typically introduced into both types of sequences. After amplification, the two species are separated and the amount of detectable group incoporated into each species is determined. This detection procedure is performed for each member of the dilution series. A competition curve can then be generated and the amount of sample sequence can be extrapolated based on the known amounts of standard sequence.

Methods of competitive amplification have been described in U.S. Pat. No. 5,219,727; Jalava et al., *BioTechniques* 15:134–39 (1993). While these competitive amplification techniques have shown utility, they require substantial amounts of sample preparation time as well as technician interaction and concomitant risk of sample contamination. In addition, performing amplification on members of a dilution series requires more reagents than performing amplification on a single sample. All of these factors add to the costs of performing competitive amplification reactions.

Moreover, all prior art methods involve PCR amplification wherein the middle part of the standard sequence is completely unrelated to the target sequence to be detected, and is flanked by target-specific primers to used to differentiate the standard from the target sequence. Thus, the two sequences are easily differentiated. Such a method is incompatible with LCR amplification because the middle pan of both the target and standard sequences is critical to the success of the amplification reaction. No prior art method existed, prior to Applicant's invention, for differentiating a standard sequence from a target sequence using LCR amplification.

Thus, there is a need for a method of quantitatively performing an amplification reaction, wherein the middle pan of the standard sequence is substantially similar to the target sequence, which does not require amplifying a series of concentration standards alongside each assay to be quantitated, and can be employed in a clinical laboratory setting.

SUMMARY OF THE INVENTION

The present invention provides a method for detecting the amount of a target nucleic acid sequence which may be present in a test sample comprising the steps of:

(a) contacting said test sample with means for performing a nucleic acid amplification reaction and:
  (i) two target primer sets, wherein a first primer set represents a first target sequence and a second primer set represents a second target sequence within the genome of the target nucleic acid, and wherein each primer set comprises four oligonucleotide primers of which two are sense primers and the other two are antisense primers, (ii) an internal standard (IS) sequence, wherein the IS sequence is substantially derived from a combination of the first target sequence and the second target sequence, (iii) an IS primer set, wherein the IS primer set comprises four oligonucleotide primers of which two are derived from the first target sequence and the other two are derived from the second target sequence, and (iv) a set of dNTPs, under hybridizing conditions such that, for each pair of target oligonucleotide primer sequences or IS oligonucleotide primer sequences which hybridizes to each strand of said target sequences or said IS sequence or its complementary strand, a ligase reaction takes place whereby the nucleotide gap between the oligonucleotide primer sequences is filled by the dNTPs in the presence of the target nucleic acid sequence, wherein each of the ligase reactions require the same set of dNTPs, or a subset thereof, to fill the gap; and (b) determining the ratio of target amplification products to IS amplification products present in the test sample.

The method of the invention described above also can be used to distinguish between two different nucleic acid sequences which may be present in a test sample, particularly where one of the two nucleic acid sequences comprises a mutation or allele of the other nucleic acid sequence.

The invention also provides compositions for quantitatively detecting the DNA of hepatitis B virus which may be present in a sample, the composition comprising four oligonucleotide primers of from about 18 to about 25 base pairs having sequences sufficiently complementary to either a first target sequence or second target sequence within the HBV genome. Also provided are compositions for distinguishing between the wildtype and mutant DNA of hepatitis B comprising codon 145 of the HBV S-gene and/or codon 28 of the HBV precore antigen gene. Test kits comprising the compositions described above also are provided by the present invention.

DETAILED DESCRIPTION OF THE INVENTION

Figure 1:
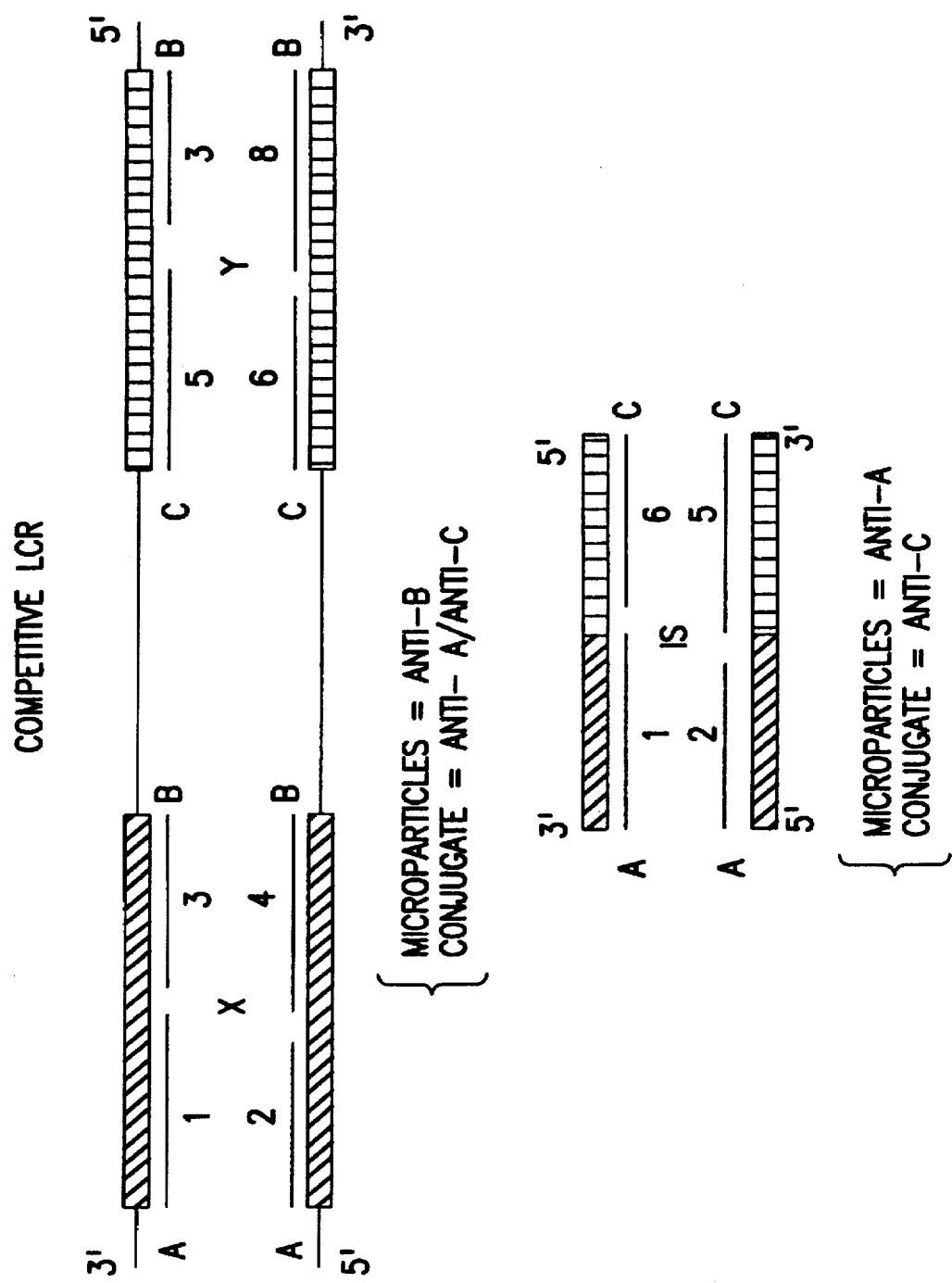
FIG. 1 is a schematic diagram of the method of the invention which depicts target sequences X and Y and their corresponding primer sets as well as an internal standard sequence and its corresponding primer set.

The method herein provided is applicable to nucleic acid amplification reactions (hereinafter "amplification reactions") which employ palmer sets (also referred to as "probe sets") to amplify a target nucleic acid sequence. Briefly, the method uses two target primer sets, each primer set representing a different target sequence within the genome of the target nucleic acid sequence, i.e., a first target sequence and a second target sequence, in an amplification reaction to quantitatively detect the concentration of a target sequence which may be present in a test sample. Additionally, the method uses an internal standard (IS) sequence which comprises a sequence substantially derived from a combination of the first target sequence and the second target sequence and its corresponding IS primer set.

In the method, the two target sequences and the IS sequence compete for the same oligonucleotide primers which comprise the target and IS primer sets. The method generally comprises contacting a test sample suspected of containing a target sequence with two target primer sets, an IS sequence and its corresponding IS primer set and dNTPs under hybridizing conditions to form a reaction mixture. The reaction mixture is cycled to allow oligonucleotide primer sequences to hybridize with, and thus, amplify the corresponding target sequences or IS sequence and its complementary strand via a ligase reaction. The presence of any amplified target sequences or IS sequences can then be detected.

A target primer series comprises two primer sets, each set of primers representing a different target sequence within the genome of the target nucleic acid sequence. A first primer set represents a first target sequence and a second primer set represents a second target sequence. In the description of the invention, the first target sequence is referred to as "Target X" and the second target sequence is referred to as "Target Y." Each target primer set comprises four oligonucleotide primers of which two are sense primers and the other two are antisense primers.

The IS sequence is substantially derived from a combination of the first target sequence and the second target sequence of the target nucleic acid. As used in the method of the invention, the IS sequence can be single-stranded or double-stranded. The corresponding IS primer set also comprises four oligonucleotide primers of which two are derived from the first target sequence and the other two are derived from the second target sequence.

In an alternative embodiment, the method of the invention can be used to quantitatively detect only one of the two target sequences X and Y by employing the oligonucleotide primers specific for the particular target sequence to be detected, an IS sequence and its corresponding IS primer set. In the amplification reaction, the target sequence X or Y and the IS sequence compete for the same two shared oligonucleotide primers which comprise the primer sets of target sequences X or Y, respectively, and the internal standard. The other two oligonucleotide primers of the IS primer set can be any sequence which will effectively participate in LCR while at the same time not interfere in the amplification of the target sequence to be detected.

A test sample is typically any component of an individual's body which can contain a target nucleic acid sequence of interest. Test samples can be prepared using methodologies well known in the art such as by taking a specimen from a patient and, if necessary, disrupting any cells contained therein to release nucleic acids.

A target nucleic acid sequence is generally a nucleic acid sequence (e.g., RNA or DNA) comprising at least two target sequences to which members of the target primer series hybridize. In the case of RNA target sequences, it will be understood that a cDNA copy of the RNA target sequence is synthesized before the amplification reaction. In a preferred embodiment of the invention, both target sequences and, thus, their corresponding primer sets characteristically are found within the genome of the target nucleic acid sequence. This feature of the invention provides the advantage of reducing the risk that the target nucleic acid sequence would not be detected in the amplification reaction due to either of the first or second target sequences being deleted or otherwise altered in the test sample. Furthermore, typically both primer sets represent target sequences that are highly conserved in the genome of the target nucleic acid to be detected. This feature of the invention provides the advantage of reducing the risk that the target nucleic acid sequence would not be detected in the amplification reaction due to the presence of a variant sequence in the test sample. For example, when the nucleic acid sequence to be detected is from a bacterial or viral genome, the primer sets should represent target sequences from those gene products which are highly conserved between bacterial strains or viral isolates, respectively.

For example, the target sequence may comprise the genome of a virus such as Hepatitis B, and the target sequences may comprise regions characteristically present in the viral genome such as the surface antigen gene, the core antigen gene and the precore antigen gene. Alternatively, both target sequences may be found within any one region of the two regions mentioned above.

In another embodiment of the invention, the two target sequences X and Y are found within different genomes. This embodiment is particularly useful for the detection of nucleic acid sequences of related organisms. For example, in an amplification reaction for the detection of HIV, the first target sequence could be derived from a region of the HIV-1 genome and the second target sequence could be derived from the same region or, alternatively, from a different region of the HIV-2 genome.

The target nucleic acid sequence can be single stranded, double stranded, continuous, or fragmented so long as portions of it are sufficiently continuous for the individual target primer sets to hybridize and amplify any specific target sequences. While the sequence of the entire genome of the target nucleic acid sequence may not be known, it is generally the case that at least the target sequence which comprises the target primer sets is known.

Although there is no minimum length requirement of the target nucleic acid sequence to be detected in an amplification reaction, typically, each oligonucleotide primer of a primer set is composed of from about 18 to about 25 base pairs, which translates into ligated primer pairs of approximately 50 nucleotides.

A target primer series along with an IS sequence and its corresponding primer set can be employed in an amplification reaction to quantitatively determine the amount of a target sequence in a test sample. Amplification reactions such as LCR and GLCR are known in the art. These reactions typically employ primers to repeatedly generate copies of a target nucleic acid sequence which is usually a small region of a much larger nucleic acid sequence. Primers are themselves nucleic acid sequences that are complementary to regions of a target sequence and under suitable conditions hybridize or bind to the complementary regions of the target sequence. Copies of the target sequence are typically generated by the process of primer ligation which utilizes enzymes with ligase activity to ligate adjacent primer pairs. While enzymatic methods of ligation are predominant, other methods such as, for example, chemical ligation are equally suitable for use according to the present invention. The nucleotides that are added to the primers or probes, as monomers or preformed oligomers, are also complementary to the target sequence. Once the primers have been sufficiently ligated they are separated from the target sequence, usually by heating the reaction mixture to a "melt temperature" which is one where complementary nucleic acid strands dissociate. Thus, a sequence complementary to the target sequence is formed.

A new amplification cycle can then take place to further amplify the number of target sequences by separating any double stranded sequences, allowing primers to hybridize to their respective targets, ligating the hybridized primers and reseparating. The complementary sequences that are generated by amplification cycles can serve as templates for primer or probe extension to further amplify the number of target sequences. Hence, multiple copies of the target sequence and its complementary sequence are produced.

Generally, four primers, two of which are complementary to a portion of a target strand and the other two which are complementary to its complement, are employed in LCR. Other reagents employed in amplification reactions, collectively designated as means for performing an amplification reaction, are well known and include: enzyme cofactors such as magnesium; salts; nicotinamide adenine dinucleotide (NAD); and deoxynucleotide triphosphates (dNTPs) such as, for example, adenine triphosphate, guanine triphosphate, cytosine triphosphate and thymine triphosphate.

In the method of the invention, a reaction mixture preferably is cycled between about 15 and about 60 times, more preferably, between about 20 and about 45 times. It also should be noted that the concentrations of, for example, the nucleotide triphosphates, enzymes and cofactors employed in the instant method may be higher than those normally used in a typical amplification reaction.

After a target primer series, IS sequence and its corresponding primer set are employed in an amplification reaction, amplified target sequence products (also referred to as "target amplification products") and amplified IS sequence products (also referred to as "IS amplification products") can be detected. In one embodiment, the detection of amplified target sequence products is separated from the detection of amplified IS sequence products into two reactions. Alternatively, in another embodiment of the invention, the detection of target amplification products and IS amplification products are determined by one detection reaction, wherein the target amplification products and IS amplification products are labeled in such a way that the two amplification products are distinguishable. For example, the target amplification products could be attached to a fluorescent label that fluoresces at one wavelength, whereas the IS amplification products are attached to a fluorescent label that fluoresces at a second wavelength. Both wavelengths could be read in one reaction mixture.

In the embodiment of the invention where two separate reactions take place, after the amplification reaction, the amplified target sequence products and amplified IS sequence products can be detected by using unique capture reagents that are immobilized to a solid phase such that each capture reagent immobilizes a unique amplified product, i.e., target sequence X, target sequence Y or IS sequence. Alternatively, in another embodiment of the invention, a first capture reagent immobilizes the target amplification products and a second capture reagent immobilizes the IS amplification products.

Capture reagents typically comprise "specific binding pair members" which can directly or indirectly form a specific binding pair with the amplified products. As used herein, specific binding member means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens such as adamantane and carbazole which are described in U.S. application Ser. No. 08/049,888 filed Apr. 21, 1993 now U.S. Pat. No. 5,424,414 published as WO 94/29329 and U.S. Pat. application Ser. No. 08/084,495 filed Jul. 1, 1993, now U.S. Pat. No. 5,464,746 published as WO 095/03296 and antibodies specific for haptens; complementary nucleotide sequences; enzyme cofactors or substrates and enzymes; and the like. According to the embodiment being described in conjunction with FIG. 1, the capture reagent used to detect the target amplification products is different than the capture reagent used to detect the IS amplification products.

Solid phase refers to any material which is insoluble, or can be made insoluble by a subsequent reaction. The solid phase can be chosen for its intrinsic ability to attract and immobilize a binding member. Alternatively, the solid phase can retain an additional receptor which has the ability to attract and immobilize a binding member. The additional receptor can include a charged substance that is oppositely charged with respect to a binding member or to a charged substance conjugated to a binding member. As yet another alternative, the receptor molecule can be any specific binding member which is immobilized upon (attached to) the solid phase and which has the ability to immobilize another binding member through a specific binding reaction. The receptor molecule enables the indirect binding of a binding member to a solid phase material before the performance of the assay or during the performance of the assay. The solid phase thus can be, for example, latex, plastic, derivatized plastic, magnetic or non-magnetic metal, glass or silicon surface or surfaces of test tubes, microtiter wells, sheets, beads, microparticles, chips, and other configurations known to those of ordinary skill in the art. It is contemplated and within the scope of the invention that the solid phase also can comprise any suitable porous material with sufficient porosity to allow, when necessary, access by a conjugate. Microporous structures are generally preferred, but materials with gel structure in the hydrated state may be used as well. The porous structure of nitrocellulose has excellent absorption and adsorption qualities for a wide variety of reagents including binding members. Nylon also possesses similar characteristics and also is suitable. Such materials may be used in suitable shapes, such as films, sheets, or plates, or they may be coated onto or bonded or laminated to appropriate inert carriers such as paper, glass, plastic films or fabrics.

There are a variety of ways in which the amplification products may be immobilized to a solid phase. For example, the solid phase may be coated with polynucleotides which form binding pairs with the amplification products. Alternatively, the amplification products may be labeled with indirect labels which form specific binding pairs with a binding member coupled to the solid phase. It will be understood that the specific binding member coupled to the solid phase may form binding pairs with all of the amplification products that may be produced in an amplification reaction or multiple specific binding pairs coupled to the solid phase may be specific for individual amplification products, for example, target sequence X amplification products or target sequence Y amplification products. Those skilled in the art also will recognize that various methods exist and may be employed to incorporate a label into an amplification product.

After the target amplification products, if any, and IS amplication products are immobilized to the solid phase, their presence thereon can be detected using a "label." The term label refers to a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that direct labels may require additional components such as, for example, substrates, triggering reagents, light and the like to enable detection of the label. When indirect labels are used for detection, they are typically used in combination with a "conjugate." A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label.

Hence, where the amplified products which are immobilized to a solid phase carry a directly detectable label, the immobilized amplified products can be detected directly. In cases where the amplified products carry an indirect label, a conjugate comprising a binding member which is specific for the indirect label can be employed to detect the presence of the amplified product on the solid phase.

The different amplification products can be differentiated by labeling the various amplification products with differentiable labels. For example, each amplification product can be labeled, directly or indirectly, with distinct flurophores which emit light at different wavelengths. Alternatively, each amplification product can be labeled with a different enzyme each of which emits a signal in the presence of a different fluorogenic substrate. As a further alternative, the amplification products can be differentiated based upon the timing at which the labels produce a signal. Specifically, the signal from a fluorophore and enzyme can be differentiated by reading a constant signal from the fluorophore and reading a rate signal from the enzyme whereby the constant signal, if any, establishes a baseline signal from which the rate signal begins. Such a detection method has been described in co-pending U.S. patent application Ser. No. 08/362,036 filed Dec. 22, 1994, which enjoys common ownership and is incorporated herein by reference.

According to one embodiment of the invention, and with reference to FIG. 1, a test sample which may contain a target nucleic acid sequence comprising target sequences X and Y is contacted with two primer sets, the first set being specific for target X and comprising oligonucleotide primers 1, 2, 3 and 4, the second set being specific for target Y and comprising oligonucleotide primers 5, 6, 7 and 8. The test sample also is contacted at the same time with an internal standard sequence IS and its corresponding oligonucleotide primers 1, 2, 5 and 6. Haptens A, B and C are associated with the oligonucleotide primer sets in such a way that amplified target sequence products X and Y are detected by capture on microparticles to which anti-hapten antibody capture reagents are attached. In the embodiment depicted in FIG. 1, amplification products X and Y are captured by anti-B antibody and a signal is generated with a mixture of anti-A antibody and anti-C antibody conjugated with a label, for example, the enzyme alkaline phosphatase. Similarly, IS amplification products are captured by anti-A antibody and a signal is generated with anti-C antibody conjugated with a label such as alkaline phosphatase. A signal ratio of (X+Y)/S is determined to quantitate the amount of the target nucleic acid sequence contained in the sample.

In accordance with the underlying principles of the method of the invention, in the absence of X and Y target sequences, or in the presence of low levels, the degree of IS target amplification should remain constant. As the starting concentration of X and Y target sequences increases, the four oligonucleotide primers involved in IS amplification will compete for the same sequences as those for X and Y target amplification, since the same four nucleotide primers are involved in X and Y target amplification. Thus, the final level of IS amplification will progressively decrease as the starting concentration of X and Y target sequences progressively increases.

During the course of amplification, hybrid structures may form between target amplification products and IS amplification products. Such hybrids cannot participate in ligation, even though oligonucleotides with 3'-hydroxyl termini within such hybrids can still be extended by the DNA polymerase. Thus, as the levels of amplification products increase, there should be an increase in the formation of such hybrids. This in turn will reduce the amount of IS amplification product generated as compared to the amount that would have been generated had the first and second target sequences not been present. The method of the invention is designed so that the amount of IS sequence used in the amplification reaction is such that the hybrid formation does not significantly decrease the amount of X and Y amplification products generated over the course of the reaction.

The extent of hybrid formation in the reaction mixture is likely to include large networks of structures containing many oligonucleotides and amplification products. In the presence of X and Y target sequences, such hybrids may increase the sensitivity of target X and target Y detection since for each hybrid captured by anti-A antibody, there are two sets of haptens (i.e., B and C) which are detectable by a labeled conjugate. On the other hand, hybrid structures should not cause false positives because they cannot form in the absence of the target sequences.

The 5' to 3' exonuclease activity of DNA polymerase can cleave the hybrid structures described above by cutting the ligated amplification product strand to which the oligonucleotide primer being extended does not hybridize. In order for the strand to be cut by the DNA polymerase, the strand must be single-stranded upstream of the cut site (i.e., 5'). Optionally, in order for the polymerase to cut the DNA, the sequence of the strand to be cut may not be modified at the 5' end. Thus, by haptenating the 5' ends of oligonucleotide primers 4 and 5, but not haptenating the 5' ends of oligonucleotide primers 1 and 8, both strands of amplified IS sequence products would be susceptible to cleavage, while both X and Y amplified sequence products would be protected from cleavage.

The net result is that IS amplification products would be cleaved, thus lowering the signal generated by the IS amplification products, while X and Y amplification products would not be cleaved, thus maintaining the signal generated by the target amplification products and allowing their participation in subsequent cycles of amplification. Cleavage would occur during cycling and afterwards by including a final incubation at or just below the Tm of nucleotide primers 2 and 7. This would result in the presence of IS amplification products in a cleavable conformation (i.e., a forked hybrid structure in which the 5'-arm of the fork is single-stranded). It will be understood that such cleavage will not occur if the polymerase used lacks 5' to 3' exonuclease activity.

In accordance with the theory of the invention, as the signal of target sequences X and Y increases through the generation of amplification products over the course of the amplification reaction and then levels off, the IS signal would start at a constant level and then decrease due to oligonucleotide primers competition, the possible formation of non-ligatable hybrids and the possible exonuclease cleavage of IS amplification products as described above.

The amount of X and Y in a test sample can be determined by locating the signal ratio of (X+Y)/IS for the sample on a standard curve generated by plotting (X+Y)/IS versus known starting concentrations of target sequences X and Y in the amplification reaction. By determining the ratio of the signal generated by the target amplification products (X+Y) to the signal generated by the IS amplification products, one can derive the original amount of X and Y targets in the test sample.

The following examples are provided to further illustrate the present invention and are not intended to limit the scope of the invention.

EXAMPLES

Example 1

QUANTITATIVE LCR AMPLIFICATION OF HBV

Two target sequences were co-amplified with an IS target sequence using GLCR amplification. One target sequence, target sequence X (SEQ ID No. 1) although presented as a single strand for simplicity, was actually used in duplex form. SEQ. ID. No. 1 corresponds to map positions 180 to 225 of the hepatitis B virus (HBV) as reported by Ono et at., Nucleic Acids Research 11:1747–57 (1983). The other target sequence, target sequence Y (SEQ ID No. 2), which also is presented as a single strand, also was employed in duplex form. SEQ ID No. 2 corresponds to map positions 658 to 703 of HBV. The insert was cloned from HBV subtype ay. Both sequences are shown below in Table 1 in a 5' to 3' direction.

TABLE 1

| SEQ. ID. No. | 5'-Sequence-3' |
| --- | --- |
| 1 | T AGGAC C C CT GCT C GT GT T AC AGGC GGGGT T T T T C T T GT T GAC AAG |
| 2 | C CGT T T C T C C T GGC T C AGT T T ACT AGT GC C AT T T GT T C AGT GGT T C |

A linearized double-stranded recombinant DNA plasmid Y82-1 was constructed which contained the X and Y target sequences from the vector pUC19. The HBV insert was derived from a BamHI fragment of the HBV genome, approximately 1400 base pairs long, comprising the entire surface antigen gene (S-gene), a portion of the pre-S gene and a little of the X gene.

Target-specific probes were designed to amplify and detect the above target sequences by LCR. The first primer set was specific for SEQ ID No. 1 and its complementary strand. Two probes from this set (SEQ ID No. 3 and SEQ ID No. 4) were haptenated with biotin which is designated "Bio". The remaining two probes from this set (SEQ ID No.

5 and SEQ ID No. 6) were haptenated with fluorescein which is designated "Fl". The 5' ends of SEQ ID No. 4 and SEQ ID No. 5 were functional with a phosphate group, which is designated "p", to allow ligation of SEQ ID No. 3 to SEQ ID No. 5 and ligation of SEQ ID No. 4 to SEQ ID No. 6. SEQ ID No. 4 and SEQ ID No. 6 hybridized with SEQ ID No. 1, and SEQ ID No. 3 and SEQ ID No. 5 hybridized with SEQ ID No. 1's complementary strand. The probe set employed to amplify and detect target sequence X is shown in Table 2 where individual probes are listed in a 5' to 3' direction.

TABLE 2

| SEQ. ID. No. | 5'-Sequence-3' |
| --- | --- |
| 3 | BioTAGGACCCCTGCTCGTGTTACA |
| 4 | pAACACGAGCAGGGGTCCTABio |
| 5 | pCGGGGTTTTTCTTGTTGACAAGFl |
| 6 | FlCTTGTCAACAAGAAAAACCCCGCC |

A second primer set was specific for SEQ ID No. 2 and its complementary strand. Two probes from this set (SEQ ID No. 7 and SEQ ID No. 8) were haptenated with adamantane which is designated "Ad". The remaining two probes from this set (SEQ ID No. 9 and SEQ ID No. 10) were haptenated with fluorescein (Fl). The 5' ends of SEQ ID No. 8 and SEQ ID No. 9 were functional with a phosphate group (p) to allow ligation of SEQ ID No. 7 to SEQ ID No. 9 and ligation of SEQ ID No. 8 to SEQ ID No. 10. SEQ ID No. 8 and SEQ ID No. 10 hybridized with SEQ ID No. 2, and SEQ ID No. 7 and SEQ ID No. 9 hybridized with SEQ ID No. 2's complementary strand. The probe set employed to amplify and detect target sequence Y is shown in Table 3 where individual probes are listed in a 5' to 3' direction.

TABLE 3

| SEQ. ID. No. | 5'-Sequence-3' |
| --- | --- |
| 7 | AdCCGTTTCTCCTGGCTCAGTTTAC |
| 8 | pAAACTGAGCCAGGAGAAACGGAd |
| 9 | pAGTGCCATTTGTTCAGTGGTTCFl |
| 10 | FlGAACCACTGAACAAATGGCACTA |

An internal standard target sequence was synthesized which comprised a chimera of the 5'-half of the X sequence and the complementary strand of the 5 '-half of the Y sequence. The IS target used was single-stranded. The sequence is shown below in Table 4 in a 5' to 3' direction.

TABLE 4

| SEQ. ID. No. | 5'-Sequence-3' |
| --- | --- |
| 11 | T AGGAC C C CT GC T C GT GT T AC AGT AAAC T GAGC C AGGAGAAAC GG |

The primer set specific for SEQ ID No. 11 and its complementary strand consisted of the four oligonucleotide primers SEQ ID No. 3, SEQ ID No. 4, SEQ ID No. 7 and SEQ ID No. 8.

The plasmid Y82-1, containing the X and Y target sequences as described above, was tested at eight different concentrations in the reaction, as set forth in Table 5 below, to co-amplify the target sequences according to GLCR essentially as described in EP-A-439,182. Concentrated 5× LCR buffer used in the reaction comprised 250 mM EPPS buffer, pH 7.8, 50 mM $MgCl_2$, 50 mM $NH_4Cl$, 400 mM $K^+$ and 50 ug/ml bovine serum albumin (BSA). LCR "Master Solution" comprised the following components:

| Component | Final Concentration |
| --- | --- |
| 34 ul dGTP (50 uM) | 1 um |
| 34 ul dGTP (50 mM) | 1 um |
| 17 ul beta-NAD (10 mM) | 100 um |
| 4.25 ul oligonucleotide primer SEQ ID No. 3 | $2.5 \times 10^{10}$/ul |
| 4.25 ul oligonucleotide primer SEQ ID No. 4 | $2.5 \times 10^{10}$/ul |
| 4.25 ul oligonucleotide primer SEQ ID No. 5 | $2.5 \times 10^{10}$/ul |
| 4.25 ul oligonucleotide primer SEQ ID No. 6 | $2.5 \times 10^{10}$/ul |
| 4.25 ul oligonucleotide primer SEQ ID No. 7 | $2.5 \times 10^{10}$/ul |
| 4.25 ul oligonucleotide primer SEQ ID No. 8 | $2.5 \times 10^{10}$/ul |
| 4.25 ul oligonucleotide primer SEQ ID No. 9 | $2.5 \times 10^{10}$/ul |
| 4.25 ul oligonucleotide primer SEQ ID No. 10 | $2.5 \times 10^{10}$/ul |
| 6.8 ul IS target sequence DNA (100 copies/ul) | 20 copies/LCR |
| 340 ul 5X LCR buffer | |
| 945.2 ul $H_2O$ | |

The enzyme solution comprised the following components:

| Component | Units/LCR |
| --- | --- |
| 175 ul Abbott ligase (1360 units/ul) | 6800 |
| 14 ul Amplitaq® polymerase (5 units/ul) | 2 |
| 21 ul 1X LCR buffer | |

The Abbott ligase is commercially available from Abbott Laboratories, Abbott Park, Ill. The Amplitaq® polymerase is commercially available from Cetus Corporation, Emeryville, Cailf. 2.5 ul Y82-1 was added to 41.5 ul LCR Master Solution. The mixture was mixed and then centrifuged using a microfuge for several seconds to settle the mixture. One drop of mineral oil was added to each reaction mixture, and the mixture was heated to 100° C. for three minutes and centrifuged again. The mixture was allowed to cool to 75° C., then six ul enzyme solution was added to obtain a final volume of 50 ul. Each 50 ul reaction was performed in triplicate. Thermal cycling was performed in a COY Tempcycler, commercially available from Coy Laboratory Products, Inc., Ann Arbor, Mich., for 40 cycles of 85° C. for 30 seconds and 54° C. for 60 seconds. After thermocycling, all three replicates were combined. The combined LCR pool was divided in half and analyzed in two separate IMx assays. Each IMx assay was run in duplicate. The first IMx assay (IMx-1) was designed to detect HBV X and Y target sequences. Specifically, 35 ul of each combined LCR pool were added to 35 ul of IMx line diluent, commercially available from Abbott Laboratories. Micropar-ticles to which anti-fluorescein antibody was attached captured the oligonucleotides which were detected with conjugate that contained a 50/50 ratio of anti-biotin antibody and anti-adamantane antibody conjugated to alkaline phosphatase (AP). The second IMx assay (IMx-2) was designed to detect the IS target sequence. Thirty-five ul of each combined LCR pool were added to 35 ul of IMx line diluent. Microparticles to which anti-biotin antibody was attached captured the oligonucleotides which were detected with conjugate that contained anti-adamantane antibody conjugated to AP. IMx results for each LCR pool are reported below.

TABLE 5

| LCR Pool No. | Y82-1 Molecules | IMx-1 | IMx-2 |
|---|---|---|---|
| 1 | $10^7$ | 1568 | 49 |
| 2 | $10^6$ | 1523 | 206 |
| 3 | $10^5$ | 1377 | 523 |
| 4 | $10^4$ | 990 | 778 |
| 5 | $10^3$ | 645 | 924 |
| 6 | $10^2$ | 398 | 1058 |
| 7 | $10^1$ | 177 | 1123 |
| 8 | 0 | 19 | 1180 |

A log:log plot of Y82-1 molecules versus the ratio of IMx-1/IMx-2 showed that the quantitation of the target nucleic acid sequence was linear over five orders of magnitude.

Example 2

Detection of Wild-Type and Mutant Forms of HBV Precore Gene and Surface Antigen Gene The method of the invention can be used to distinguish between the wild-type (Wt) and mutant (Mut) sequences for the HBV surface antigen (HBsAg) codon 145 mutation. Codon 145 of the HBsAg gene codes for the amino acid glycine. However, a point mutation within this codon changes the amino acid to arginine, resulting in a vaccine escape phenotype. The Wt sequence (SEQ ID No. 12), although presented as a single strand for simplicity, is used in duplex form. The point mutations of the mutant sequence (SEQ ID No. 13) is presented in bold-type. Target-specific probes are designed to amplify and detect the Wt and Mut target sequences by LCR, as set forth in Table 6 below. The primer set which is specific for SEQ ID No. 12 and its complementary strand comprises SEQ ID No. 14, SEQ ID No. 15, SEQ ID No. 16 and SEQ ID No. 17. The 5' ends of SEQ ID No. 15 and SEQ ID No. 16 are functional with a phosphate group (p) to allow ligation of SEQ ID No. 14 to SEQ ID No. 16 and ligation of SEQ ID No. 15 to SEQ ID No. 17. SEQ ID No. 18 is replaced for SEQ ID No. 14 for the mutant sequence SEQ ID No. 13.

Similarly, the method of the invention can be used to detect a point mutation within codon 28 of the HBV precore antigen (HBeAg) gene. Codon 28 codes for the amino acid tryptophan. However, a point mutation within this codon changes the amino acid to a stop codon, resulting in a HBeAg-phenotype. An often-associated second mutation occurs three bases further downstream. The Wt sequence (SEQ ID No. 19), although presented as a single strand for simplicity, is used in duplex form. The point mutations of the mutant sequence (SEQ ID No. 20) are presented in bold-type. Target-specific probes are designed to amplify and detect the Wt and Mut sequences by LCR, as set forth in Table 6 below. The primer set which is specific for SEQ ID No. 19 and its complementary strand comprises SEQ ID No. 21, SEQ ID No. 22, SEQ ID No. 23 and SEQ ID No. 24. The 5' ends of SEQ ID No. 22 and SEQ ID No. 23 were functional with a phosphate group (p) to allow ligation of SEQ ID No. 21 to SEQ ID No. 23 and ligation of SEQ ID No. 22 to SEQ ID No. 24. Oligonucleotide primer SEQ ID No. 25 is replaced for primer SEQ ID No. 21 for the single point mutation.

The IS sequence is shown as SEQ ID No. 26 in Table 6 below. The primer set specific for SEQ ID No. 26 and its complementary strand comprises the four oligonucleotide primers SEQ ID No. 16, SEQ ID No. 17, SEQ ID No. 23 and SEQ ID No. 24. To perform competitive LCR for the HBsAg gene, oligonucleotides listed above for the target sequence one wishes to detect, either the Wt or Mut sequence, are used along with oligonucleotides SEQ ID No. 23 and SEQ ID No. 24. To perform competitive LCR for the HBeAg gene, oligonucleotides listed above for the target sequence one wishes to detect, either the Wt or Mut sequence, are used along with oligonucleotides SEQ ID No. 16 and SEQ ID No. 17.

Alternatively, both HBsAg and HBeAg competitive LCR assays can be performed together, preferably both Wt assays or both Mut assays together, since they share the same nucleotide requirements. In this case, the IS will always be amplified because oligonucleotide primers SEQ ID No. 16, SEQ ID No. 17, SEQ ID No. 23 and SEQ ID No. 24 will always be present. No additional dNTPs are required for gap filling on the IS because only dGTP is required which already would be present in the other LCR assays.

TABLE 6

| SEQ. ID. No. | 5'-Sequence-3' |
|---|---|
| 12 | C T GT AC C AAAC C T T C GGAC GGAAAT TGC ACC T GT AT T C C C AT C C C |
| | 5'-Sequence-3' |
| 13 | C T GT AC C AAAC C T T C GGAC AGAAAT TGC ACC T GT AT T C C C AT C C C |
| 14 | FI CTGTACCAAACCTTCGGAC |
| 15 | p TCCGAAGGTTTGGTACAGFI |
| 16 | p AAATTGCACCTGTATTCCCATCCCBi o |
| 17 | Bi o GGGATGGGAATACAGGTGCAATTTC |
| 18 | FI CTGTACCAAACCTTCGGACA |
| 19 | T GT GC C T T GGGT GGC T T T GGGGCAT GGAC AT T GAC CC T T AT AAA |
| 20 | T GT GC C T T GGGT GGC T T T AGGAC AT GGAC AT T GAC CC T T AT AAA |
| 21 | FI TGTGCCTTGGGTGGCTTTG |
| 22 | p AAAGCCACCCAAGGCACAFI |

TABLE 6-continued

| | |
|---|---|
| 23 | p CATGGACATTGACCCTTATAAAAd |
| 24 | Ad TTTATAAGGGTCAATGTCCATGCCC |
| 25 | Fl TGTGCCTTGGGTGGCTTTA |
| 26 | GGGATGGGAATACAGGTGCAATTTCGGGCATGGACATTGACCCTTATAAA |

Using the IMx format as described in Example 1, the Wt and Mut HBsAg amplification products would be captured on anti-fluorescein microparticles and detected with anti-biotin conjugate. The Wt and Mut HBeAg amplification products would be captured on anti-fluorescein particles and detected with anti-adamantane conjugate. To test for HBsAg amplificaton products and HBeAg amplification products in one reaction, a mixture of anti-adamantane and anti-biotin conjugate would be used. In a second IMx test, the co-amplified IS products, present in all reactions, would be captured on anti-biotin microparticles and detected with anti-adamantane conjugate. In this way, the IS products would be specifically detected and compared to the IMx signal of the target sequences being tested as described in Example 1.

| LCR Test | SEQ ID No. | Hapten | dNTPs Required |
|---|---|---|---|
| HBeAg-Wt | 21, 22 | Fl | G, C |
|  | 23, 24 | Ad |  |
| HBeAg-Mut | 25, 22 | Fl | G, T |
|  | 23, 24 | Ad |  |
| HBsAg-Wt | 14, 15 | Fl | G, C |
|  | 16, 17 | Bio |  |
| HBsAg-Mut | 18, 15 | Fl | G, T |
|  | 16, 17 | Bio |  |
| IS Target | 23, 24 | Ad | G only |
|  | 16, 17 | Bio |  |

While the invention has been described in detail and with reference to specific embodiments, it will be apparent to one skilled in the art that various changes and modifications may be made to such embodiments without departing from the spirit and scope of the invention.

---

What is claimed is:

1. A method for detecting the amount of at least one target nucleic acid sequence which may be present in a test sample, comprising the steps of:
(a) performing a nucleic acid amplication reaction with said test sample by contacting said test sample with:
(i) two target primer sets, wherein a first primer set represents a first target sequence and a second primer set represents a second target sequence within the genome of the target nucleic acid sequence, and wherein each primer set comprises four oligonucleotide primers of which two are sense primers and the other two are antisense primers,
(ii) an internal standard (IS) sequence, wherein the IS sequence comprises a chimeric molecule wherein said chimeric molecule comprises a sequence from either a first or second half of one of the target nucleic acid sequences and wherein the sequence of said chimeric molecule is colinear with a sequence from either the first or second half of the other target nucleic acid sequence such that a combination of the first target nucleic acid sequence and the second target nucleic acid sequence is formed,
(iii) an IS primer set, wherein the IS primer set comprises four oligonucleotide primers of which two are derived from the first target nucleic acid sequence and the other two are derived from the second target nucleic acid sequence, and
(iv) a set of dNTPs, under hybridizing conditions such that, for each pair of target oligonucleotide primer sequences or IS oligonucleotide primer sequences which hybridizes to each strand of said target nucleic acid sequences or said IS sequence or its complementary strand, a ligase chain reaction takes place whereby a nucleotide gap between the oligonucleotide primer sequences is filled by DNA polymerase in the presence of said dNTPs and in the presence of the target nucleic acid sequence, wherein each of the polymerase reactions require the same set of dNTPs, or a subset thereof, to fill the nucleotide gap resulting in juxtaposed 3' and 5' ends which are joined by DNA ligase, and (b) determining the ratio of target amplification products to IS amplification products present in the test sample as a measure of the amount of target nucleic acid sequence present in the test sample.

2. The method of claim 1 wherein the amplification reaction comprises between about 15 and 60 thermal cycles.

3. The method of claim 1 wherein at least one member of each of said primer sets includes a label.

4. The method of claim 3 wherein said label is indirectly detectable.

5. The method of claim 1 wherein said determining step comprises the steps of:

(a) immobilizing said target amplification products and IS amplification products to a solid phase using capture reagents such that a first capture reagent immobilizes the target amplification products and a second capture reagent immobilizes the IS amplification products; and (b) detecting a signal generated by the presence of target amplification products or IS amplification products.

6. The method of claim 5 wherein said capture reagents comprise a member of a specific binding pair wherein the binding member specifically binds to a specific binding pair member attached to said amplification product.

7. The method of claim 1, wherein one of the two target nucleic acid sequences comprises a mutation or allele of the other nucleic acid sequence when two nucleic acid sequences are tested.

8. The method of claim 7, wherein said mutation or allele is a mutation of HBV DNA comprising codon 145 of the HBV S-gene, and wherein said other nucleic acid sequence is wild type HBV.

* * * * *